United States Patent [19]

DeLacy

[11] Patent Number: 4,494,408
[45] Date of Patent: Jan. 22, 1985

[54] METHOD AND APPARATUS FOR NON-DESTRUCTIVE TESTING OF COMPOSITE MATERIALS

[75] Inventor: Thomas J. DeLacy, Los Altos, Calif.

[73] Assignee: Ford Aerospace & Communications Corporation, Detroit, Mich.

[21] Appl. No.: 402,450

[22] Filed: Jul. 27, 1982

[51] Int. Cl.³ .............................................. G01N 29/04
[52] U.S. Cl. ......................................... 73/587; 73/599
[58] Field of Search ................. 73/587, 597, 599, 658; 374/16

[56] References Cited

U.S. PATENT DOCUMENTS

| Re. 29,886 | 1/1979 | Dembiak et al. | 364/469 |
|---|---|---|---|
| 3,442,756 | 5/1969 | Lehtinen | 73/599 |
| 3,819,915 | 6/1974 | Smith . | |
| 3,985,712 | 10/1976 | Garst . | |
| 4,007,631 | 2/1977 | Saifi et al. | 73/658 |
| 4,022,555 | 5/1977 | Smith . | |
| 4,237,538 | 12/1980 | LeDall | 364/500 |
| 4,275,448 | 6/1981 | LeDall | 364/500 |

OTHER PUBLICATIONS

"Characterization of Stability Mechanisms . . . " by DeLacy et al., Oct. 1982, from Proceedings of the 1981 Defense Advanced Research Projects Agency Conference, pp. 1–6.

*Primary Examiner*—James J. Gill
*Attorney, Agent, or Firm*—Kenneth R. Allen; Edward J. Radlo; Robert D. Sanborn

[57] ABSTRACT

Methods and apparatus are disclosed for monitoring and controlling potential residual stress relief mechanisms in composite epoxy resin materials. Passive and injected, or active, acoustic signals originating in or propagated through a specimen material during the formation process produce signatures identifiable with known residual stress relief mechanisms. Real-time control of material temperature and external pressure during formation in response to acoustic signals measured or observed in relation to desired acoustic signature minimizes formation of undesired material properties.

22 Claims, 4 Drawing Figures

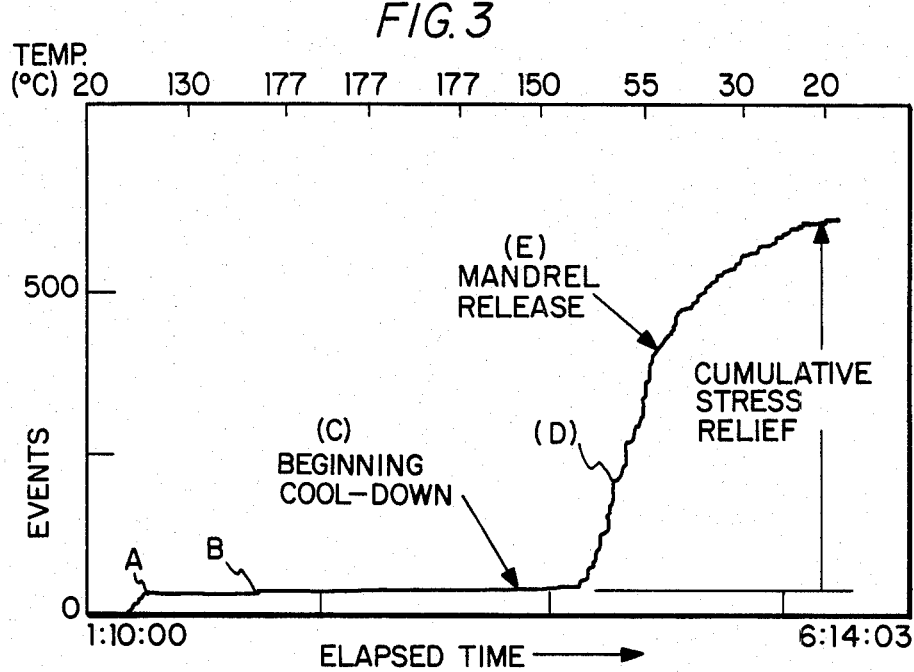
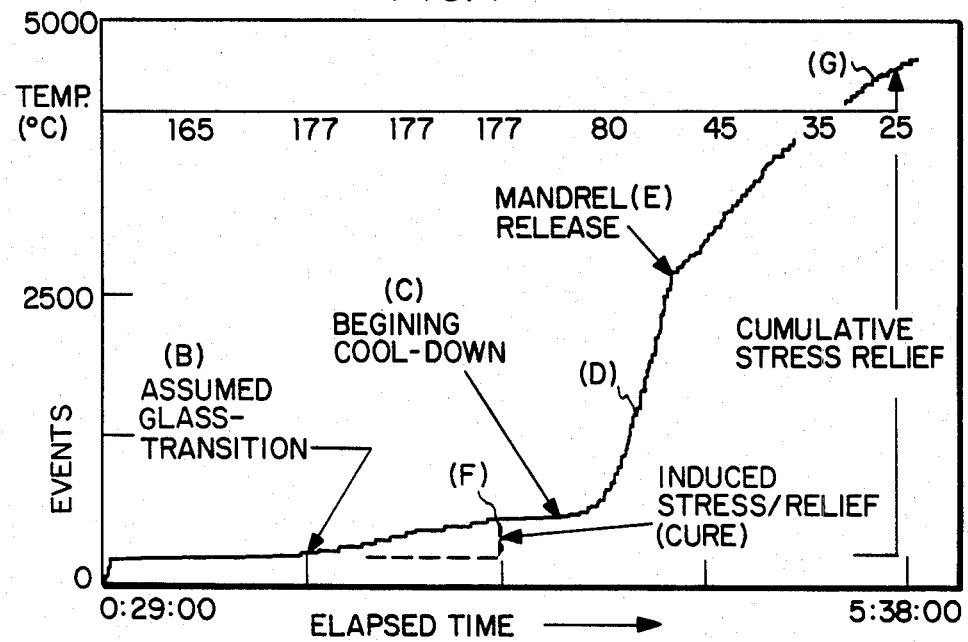

METHOD AND APPARATUS FOR NON-DESTRUCTIVE TESTING OF COMPOSITE MATERIALS

BACKGROUND OF THE INVENTION

1. Field of Invention

This invention relates to acoustic analysis of plastic composition materials such as graphite and fiber reinforced epoxy materials. In particular, the invention relates to a method and apparatus for determining and controlling potential dimensional stability, including relaxation stress potential, of composite materials through the use of acoustic sensing techniques during solidification and subsequent thermal loading.

Advanced composite materials, primarily graphite and aramid fiber reinforced epoxy resin materials, are attractive to a number of applications due to their high specific stiffness, high strength and very low coefficients of thermal expansion. Among the applications are spacecraft antennas and microwave components, which impose stringent demands on dimensional stability over a broad range of operating temperature and stress conditions. However, such composite materials are heterogeneous as well as anisotropic. Consequently, thermal treatment, including thermal loading during and subsequent to formation of the solid state of the material, induces internal residual stresses. The stresses are subject to relaxation with time, which result in dimensional modification, the extent of which may be unacceptable in certain critical applications, such as spacecraft antenna systems. Therefore, great interest exists in predicting conditions for stress relief and in determining the effect of preconditioning thermal treatments on dimensional stability of composite materials.

2. Description of the Prior Art

The following patents were uncovered in a search of the public records of the U.S. Patent and Trademark Office respecting the subject invention:

Garst, U.S. Pat. No. 3,985,712;
Smith, U.S. Pat. No. 4,022,555; and U.S. Pat. No. 3,819,915;
Dembiak et al., U.S. Pat. No. Re. 29,886;
Le Dall, U.S. Pat. No. 4,275,448; and U.S. Pat. No. 4,237,538.

In addition, a paper has been coauthored by the inventor of the present invention after the present invention was made. The paper was presented at the Air Force/Defense Advanced Research Project Agency Review of Progress in Quantitative NDE at the University of Colorado, Boulder on Aug. 3, 1981. The paper has been published in the Proceedings of the Review in about October 1982.

The Garst patent discloses a method and apparatus for preparing polyester resins in which the resin is monitored and controlled by a computer which takes periodic temperature readings and compares the temperature readings with an empirically determined temperature/time curve stored in the computer. Heat is then either added or removed from the reactor, vessel so that reactor temperature is made to coincide with the temperature/time curve for the empirically derived ideal material state. This patent is representative of inventions which rely on temperature/time characteristics as an indirect means for analyzing and controlling the integrity of materials during formation of a solid or semisolid state. However, no suggestion is made on how to analyze or control stress-related charcteristics such as distributed defects and residual stress relief characteristics.

The Smith patents describe inventions relating to the control of vulcanization processes in which a reaction rate is assumed based on a monitored temperature. The apparatus according to the Smith patents as well as the method embodied in the apparatus fail to teach or suggest direct analysis or control of stress-related characteristics of the material being formed.

The Dembiak et al. patent discloses methods of an apparatus for controlling the thickness of an annular plastic extrusion wherein an ultrasonic reflected signal is used in conjunction with an appropriate positioning or function control device to control the amount of material removed.

The Le Dall patents disclose a digitally controlled process directed to the treatment of resins and are representative of the state of the art of resin process control. There is no suggestion of any mechanism for controlling stress-related characteristics.

SUMMARY OF THE INVENTION

According to the invention, a method and apparatus are provided for acoustically analyzing stress relief mechanisms in composite materials and particularly for analyzing and controlling stress relief mechanisms during formation of graphite reinforced epoxy resin materials. The invention is based on a discovery that abrupt and often disordered residual stress relief is associated with acoustic emission signatures attributable to the initiation and propagation of certain types of material characteristics which occur during material formation. Undesired defects known as macro defects, such as through-lamina cracks can be identified and minimized according to the invention by acoustic emission techniques. Desired uniform stability is identified by a different acoustic emission signature. Typically low and evenly distributed energy releases emit or propagate characteristic acoustic emissions associated with the formation of certain micro mechanisms which dissipate the stress within a material.

Relaxation of internal residual stresses in composite materials may result in undesired changes in dimensional stability. Acoustic detection according to the invention is useful in predicting conditions which accompany or initiate stress relief during material formation and in determining and in controlling the effect of preconditioning thermal treatments on dependent dimensional stability.

According to specific embodiments of the invention, an active transducer means, such as an active acoustic excitation source and an acoustic sensor which is sensitive to signals injected into the material by the excitation source, and passive transducer means, typically passive transducer sensors sensitive primarily to acoustic signals generated by relaxation of stress mechanisms within the subject composite material, are employed in combination to record signatures characteristics of the specimen material during elevated temperature formation of a solid state of the material and/or during post-cure cool-down. The apparatus may also be used during subsequent thermal cycling to further analyze the specimen material. Template signatures may be defined for use as a reference standard from which an error signal can be generated in a closed loop feedback system for controlling the formation process. A signature may be defined in terms of stress relief events manifest in the form of acoustic signals having characteristic amplitude and frequency spectra. In a closed loop system, pressure and temperature may be modulated with time by examining acoustic signatures and generating control signals to minimize undesired stress relief events which tend to degrade dimensional stability.

One of the purposes of the invention is to provide acoustic sensing techniques rather than temperature techniques for analyzing composite materials and for controlling the formation, i.e., curing and cooling of composite materials, such as graphite fiber reinforced epoxy resin materials.

Another purpose of the invention is to provide means for employing acoustic analysis to determine present and potential stress distribution within specific composite material specimens and to correlate associated stress relaxation with dimensional stability and potential failure mechanisms of the specimens.

Another purpose of the invention is to employ acoustic analysis to examine glass transition and cure parameters which influence stress energy and potential residual stress relief mechanisms in composite materials.

Another purpose of the invention involves the use of novel acoustic emission analysis techniques to determine long term dimensional stability by relating potential residual stress relief mechanisms to stress-formed micro mechanisms and macro defects in a specimen material.

Another purpose of the invention is to provide an apparatus for real-time analysis of a composite material during the formation process.

Another purpose of the invention is to provide an apparatus for recording a multidimensional signature characteristic indicative of the dimensional stability of a specimen composite material for use in quality control and assurance and for use in grading of materials.

These and other purposes of the invention will be apparent by reference to the following detailed description taken in connection with the accompanying drawings.

BRIEF DESCRIPTION OF THE DRAWINGS

FIG. 3 is a time versus accumulated event diagram illustrating one form of a signature template for use in a method according to the invention.

FIG. 4 is a time versus accumulated event diagram illustrating one form of a signature generated by a composite material during a typical cure process.

DESCRIPTION OF SPECIFIC EMBODIMENTS

Figure 1:
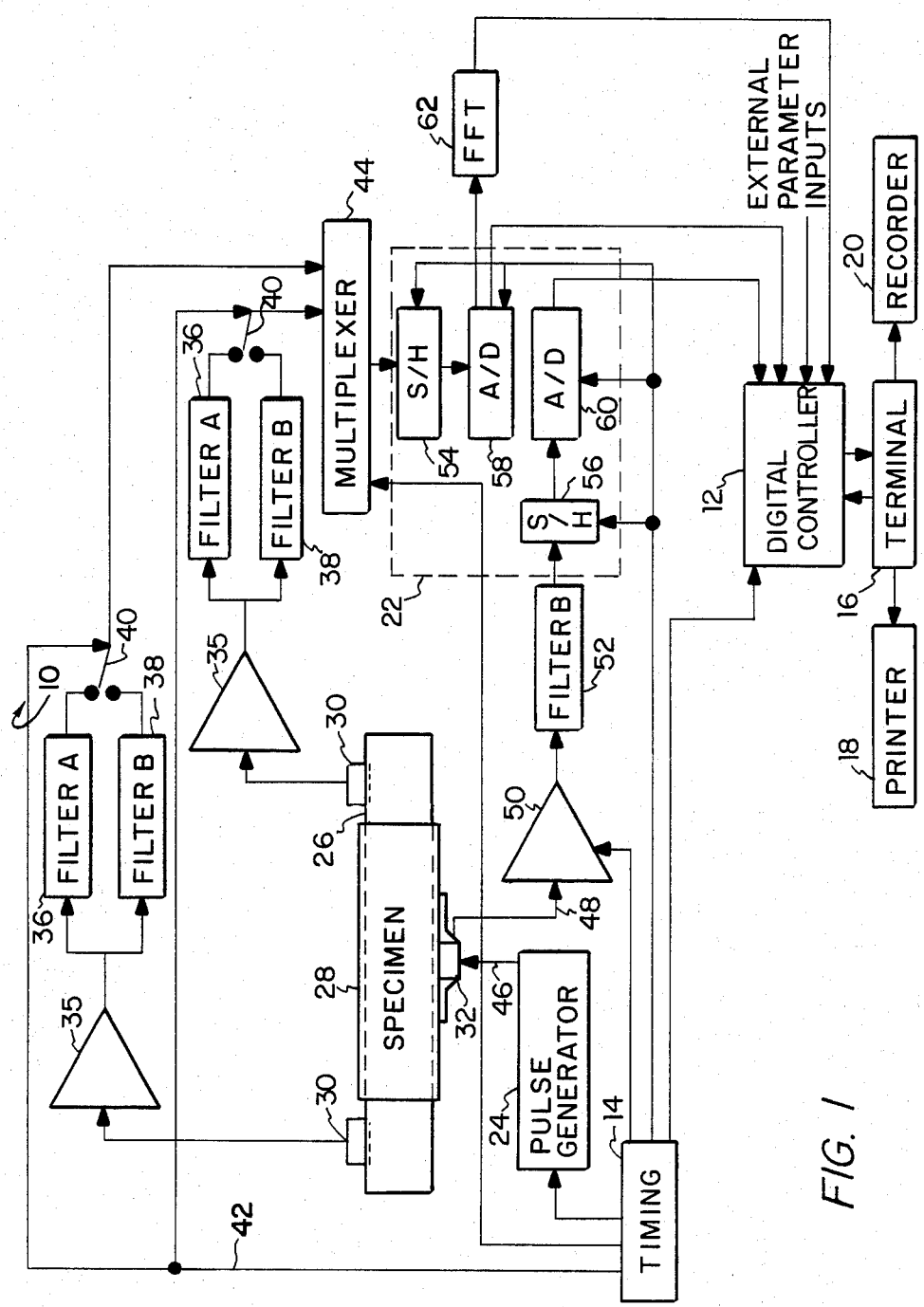
FIG. 1 is a block diagram of an apparatus for monitoring elevated temperature cure of a resin or like composite material.

FIG. 1 illustrates a specific embodiment of an apparatus for acoustic signature extraction for in situ diagnostics of graphite fiber reinforced epoxy resin thermosetting material, hereinafter referred to as composite material. A process monitoring system 10 comprises a digital controller 12, timing means 14, terminal means 16, printer means 18, recorder means 20, analog-to-digital signal converter means 22, pulse generator 24 and specimen interface means 26. The specimen interface means 26 may comprise a mandrel, such as an aluminum tube or rod within an autoclave (not shown) or like environmental chamber. Attached to the mandrel is a specimen 28 of the composite material to be monitored. Typical specimens are graphite reinforced epoxy resin systems designed for high stability applications, such as those employing low coefficient of thermal expansion (low alpha), high modulus fibers. A mandrel is used to form the specimen into a tubular shape. The material forming the specimen 28 is wrapped in layers in an uncured state about the mandrel of the specimen interface 26.

There are provided at least two types of transducers according to the invention, namely at least one and preferably two passive transducers 30 and at least one active transducer 32. The transducers 30 and 32 may be piezo-electric energy transducing devices of conventional design capable of response to acoustic energy in the 100 kHz to 500 kHz range. Each passive transducer 30 has an electrical output coupled to an amplifier 35, the output of which is directed into a filter bank consisting of a filter A 36 and a filter B 38. The outputs of the filters 36 and 38 are coupled through switching means 40 whereby the outputs of the two filters 36 and 38 may be time multiplexed under control of the timing means 14 through a timing line 42. The output of each switching means 40 is coupled into a multiplexer 44. The active transducer 32 has an active or drive input 46 from the pulse generator 24 and an output 48 to a gated amplifier 50, which is controlled by the timing means 14 so that it is on only during passive mode operation. The gated amplifier 50 is coupled through a B-type filter 52 having the same spectral characteristics as filter B 38. The output of filter 52 is coupled into the converter means 22. The converter means 22 receives analog input signals at first and second sample and hold circuits 54 and 56 from the multiplexer 44 and filter 52. The outputs of the sample and hold circuits 54 and 56 are respectively coupled into analog-to-digital converters (ADCs) 58 and 60. The sample and hold circuits 54 and 56 and the ADCs 58 and 60 are clocked by timing means 14. The outputs of the converter means 22 are coupled into the digital controller 12. Optionally, the output of the analog-to-digital converter 58 receiving signals from the passive transducers 30 is coupled through a fast Fourier transform processor 62 which is operative to extract spectral information from the time function input signals and to supply that spectral information as an input to the digital controller 12. The digital controller 12 may comprise a switching network for logging input signals, and it is responsive to timing from the timing means 14 to communicate logged input signals through the terminal means 16 to the printing means 18 and recording means 20.

The passive transducers 30 and 32 are acoustically coupled to the specimen interface means 26. For example, the mandrel portion of the specimen interface means 26, comprising an aluminum rod, may include recessed regions at each end of the mandrel into which are mounted the passive transducers 30 by means of a suitable high temperature coupling medium. The active transducer 32 may be mounted directly to the specimen 28 by a suitable high temperature medium such as any compatible tape. One example is a low-thermal expansion type of tape, such as Kapton tape.

According to the invention, the active and passive transducers 30 and 32 are used in combination for distinguishing specific events during the cure cycle of composite material and for cross correlating information to more accurately identify events in the cure cycle. For example, information which may be provided by the apparatus includes elapsed time between the beginning of the cure and the glass transition period, the flash point of the resin to a liquid state during heat-up, and separation or decoupling of the mandrel from the specimen during the cure cycle.

The invention operates as follows: During the active mode a pulse train from the pulse generator 24 synchronized by timing means 14 is injected through the active transducer 32. Specifically the active transducer 32 injects an ultrasonic acoustic wave into the specimen 28 to the passive transducers 30 attached to the specimen interface means 26. Ultrasonic signals are detected at each of the transducers 30 and 32 and amplified by amplifiers 35. The amplified signals are conveyed through filters 36, which are tailored to enhance active signals, i.e., signals which are induced by the pulse generator 24. The resultant signals are digitized and sent on to the digital controller 12 for analysis, such as signal event logging and integration. The digital controller 12 records signals so that certain critical events in the formation process are noted. For example, the digital controller 12 may sense and record information relating to the state of the resin, i.e., whether liquid or in a gelatinous form. The resultant injected signal is either transmitted through the composite specimen 28 or dampened within the short distance of the surface of the active transducer, depending upon the transient physical properties or state of the specimen. The digital controller 12 may be operative to cross correlate signals sensed through the passive transducers 30 and the active transducer 32 to sense more accurately the onset of specific events during the cure cycle.

In a typical cure cycle, an active signal, typically a pulse train, transmitted through the composite specimen 28 by the active transducer 32 is coupled to the passive transducers 30 during the initial heat up. As the resin begins gelation, the active signal transmitted through the composite falls slowly. As the resin undergoes glass transition, the active signal is observed to increase to a peak signal corresponding to the cure point of the composite.

Purely passive signals will also be observed in the composite. In the passive mode of operation, passive acoustic signals indicative of stress events in the composite may be detected. Signals from the active transducer 32 in the passive mode are directed through filter B 52 to the ADC 22. Similar acoustic signals are extracted from the passive transducers 30 and provided through multiplexer 44 to the ADC 22.

The first indication of induced stress exhibiting acoustically detectable stress events is normally a result of stress relief due to differential expansion of the mandrel (or tooling) against specimen 28 during the heat-up phase. The induced stress is observed as accompanying passive stress waves emitted by the composite as it approaches cure temperature. The event rate may be observed to correlate to characteristic amplitude and frequency spectra depending upon the nature of the associated stress-relief mechanism or mechanisms. During the cool-down portion of the cycle, strain due to mandrel shrinkage may be observed by a steep rise in the number of events recorded by passive transducers 30. The eventual loss of active signals recorded by transducers 30 is the result of acoustic decoupling which prevents the propagation of ultrasonic signals between specimen 28 and transducers 30. The decoupling may be confirmed most easily with the pickup response of transducer 32, which will show a corresponding decrease in the slope or rate of events recorded while operating in its passive mode. Both active and passive modes of operation of the apparatus are time multiplexed by switches 40 and gated amplifier 50 to permit parallel monitoring of modes by a single digital controller 12.

The thermal mechanical stability potential of the specimen 28 may be indicated by the nature of the acoustic emission from the specimen 28 during the cool-down period. Stability can be verified by observing passive acoustic emission during post-cure thermal conditioning to relieve residual stresses following cure. More particularly, the type and degree of stress relief induced in composite materials during elevated temperature cure and/or post-cure conditioning may be observed and identified using acoustic signature extraction according to the invention. During cure, stress is induced in the specimen. Once cool-down starts, the cumulative stress tends to be relieved through various relaxation mechanisms which may be identified by spectral characteristics, repetition rate characteristics and in some instances, amplitude characteristics. Generally speaking, a specimen which has been fully cured near the optimal cure temperature will exhibit a minimum number of cumulative residual stress relief events during cool-down following cure. Moreover, relatively stable cured composite materials will exhibit a minimum number of cumulative residual stress relief events during post-cure thermal cycling or subsequent thermal treatments. It has been discovered that maintenance of a cure temperature near the temperature of the assumed glass transition point minimizes the induced stress during cure. A first characteristic acoustic signature of the composite material based on stress relief events following cure and during cool-down can be used as an index to potential residual stress relief and consequent stability.

Two principal stress relief mechanisms, namely material relaxation by micro cracking and by macro cracking of the resin system, are identified with mechanisms relating to the stability of the material. For example, macro defects, namely through-lamina cracks, delaminations, and the like, may be identified by abrupt and often disordered stress relief exhibited as sharp and irregular acoustic events. Micro cracking of the resin system, which is manifest as lower amplitude more evenly distributed stress relief events, has been found to be associated with uniform structural stability. Moreover, it has been discovered that a transient stability characteristic may exist in a material for an indefinite period such that it exhibits a second characteristic acoustic signature when subjected to post-cure thermal treatments, including low-temperature soaking and/or cyclic conditioning. These two types of characteristic acoustic signatures are useful in developing standards for grading composite materials for stability. Thus, the apparatus 10 is, according to the invention, a diagnostic instrument for analyzing acoustic signature for stability analysis of composite resin materials.

Figure 2:
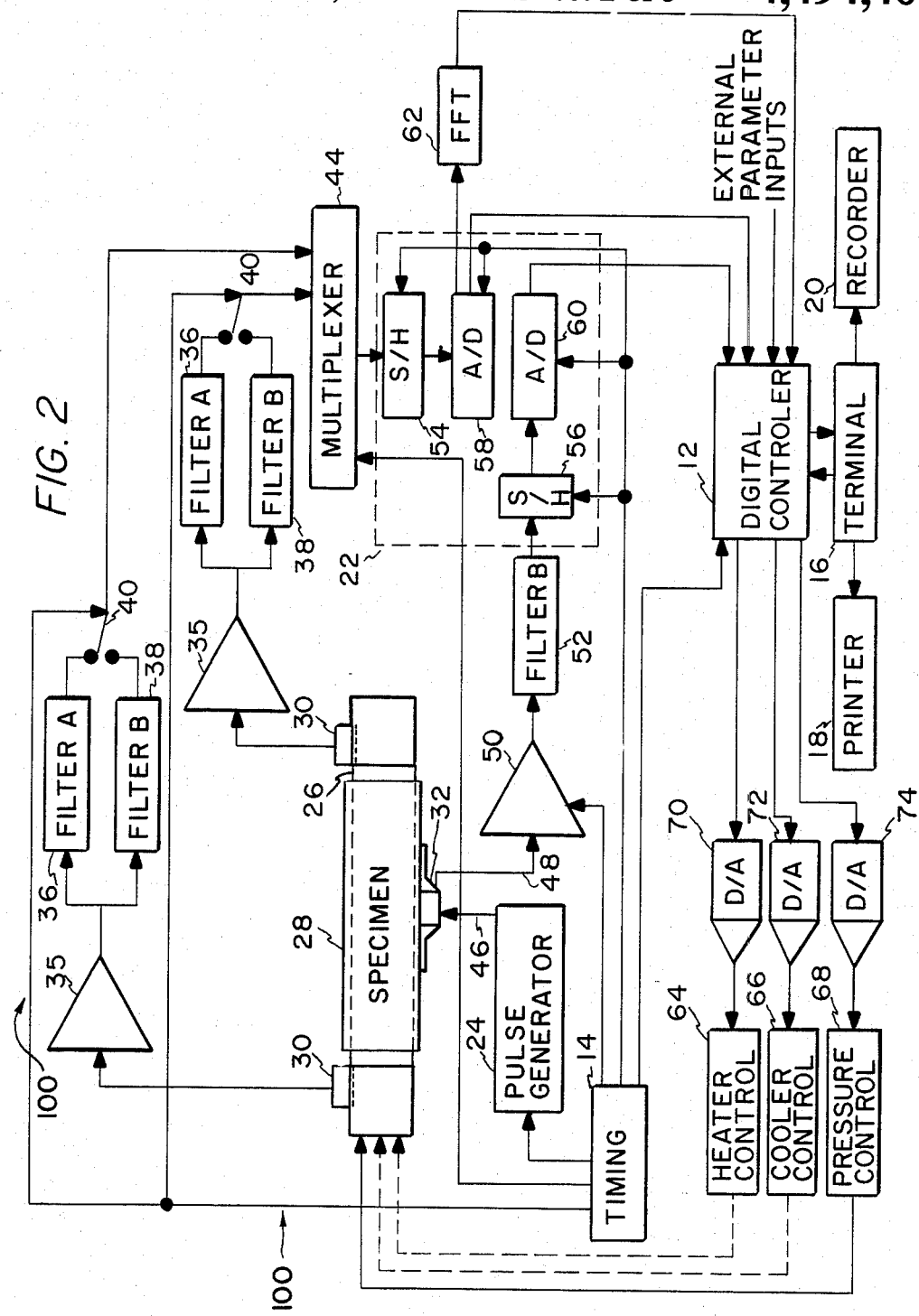
FIG. 2 is a block diagram of an apparatus for monitoring and controlling the cure process of a composite material.

Turning to FIG. 2, there is shown an alternative embodiment of the apparatus according to the invention which is useful for controlling parameters during formation of composite materials. A control apparatus 100 (FIG. 2) comprises all of the elements of the apparatus 10 (FIG. 1) plus feedback control mechanisms, including a heater control means 64, a cooler control means 66 and a pressure control means 68 coupled to the specimen interface 26. Specifically, the heater control means 64, cooler control means 66 and pressure control means 68 are operative to control autoclave parameters associated with the specimen 28. A first digital-to-analog converter means 70 is provided between the digital controller 12 and the heater control means 64. A second digital-to-analog converter means 72 is provided between the digital controller 12 and the cooler control means 66. A third digital-to-analog converter means 74 is provided between digital controller 12 and pressure control means 68.

The digital controller 12 is responsive to acoustic signals directed through the specimen 28 to control temperature and pressure applied to the specimen 28 thereby to control stress-induced events associated with the stress relief mechanisms of a composite material.

In operation, the pulse generator 24 injects signals into the specimen 28. The point of glass transition is detected through the transducers 30 and 32 causing the digital controller 12 to modulate the temperature through heater control 64 and cooler control 66. The temperature is maintained at a level which minimizes the passive event counts due to induced stress while maintaining the desired propagation characteristics of active injected signal through the specimen 28. Once complete cure has been sensed, the digital controller 12 directs heater control means 64 and cooler control means 66 to controllably decrease the temperature so as to minimize the passive event count due to cumulative stress relief on the specimen 28. The temperature is modulated to minimize the shock on the specimen 28 up to and including mandrel release, i.e., when the mandrel abruptly separates from the specimen 28, causing a loss of passive signal.

A reduced state of residual stress results from maintaining a modulated cure temperature near the glass transition point. Stresses induced by tooling expansion and minimized and internal cross linking to accommodate the structural property requirements of the specimen 28 is maximized.

Turning to FIG. 3, there is shown an exemplary signature template characteristic of a specimen which has been formed in accordance with a controlled processor 100. This figure represents only one type of signature template, namely a template consisting of cumulative stress events and stress relief events passively sensed through the sensors 30 and 32 during formation of a solid or semisolid state of composite material. The template consists of an event count over a temperature profile from 20° C. to 177° C. during an elapsed time of approximately six hours. To obtain the signature, uncured epoxy embedded with fibrous materials was mounted to a mandrel within an autoclave and then maintained at constant pressure as temperature was increased from 20° C. to 177° C. A relatively few stress relief events occurred at the outset of temperature increase, noted as point A in the cycle. At point B in the cycle, at a temperature just below 177° C., the material reaches a glass-transition state and begins to cure. (A separate active transducer signature verified the glass transition point.) Temperature was maintained close to the glass transition temperature for a preselected cure period and thereafter cooled beginning at a point C. During cure there was stress induced in the composite material as it solidified. During the cool down period following point C, the induced stress was relieved, as evidenced by an accumulation of regular micro events, as indicated in region D. The slope of region D is preferably constant, indicating that the recorded events are not erratic. Slope changes as the mandrel is released because of a partial loss of passive signals due to the separation of the mandrel from the specimen. As the specimen continued to cool the stress event rate asymtotically approached zero.

Based on subsequent thermal cycling variations in temperature were found not to induce an unacceptably high number of stress events in a properly cured specimen. In the signature for this particular type of specimen, fewer than 700 stress events were recorded during the cure cycle. A separate signature characteristic (not shown) might include a record of acoustic events injected by an active transducer whereby the propagation characteristics of the composition are recorded for changes such as the glass transition point.

In actual function, both the active transducer signature and passive transducer signature can be generated essentially simultaneously by time division multiplexing of the transducer signals.

FIG. 3 illustrates a signature of composite material during a formation process which departs from a standard signature, such as the signature of FIG. 3. The glass transition (point B) marks the beginning of an induced stress/relief stage characterizing the cure. Little effort was made to control the induced stress, which resulted in an accumulation of stress events as the mandrel expanded with temperature. As cure was completed, the number of stress events per unit time dropped off, as indicated by a point F. With the beginning of cool-down (point C), events indicating stress relief commenced, the rate of which is indicated by the slope of the integrated cumulative stress relief (point D). Mandrel release (point E) is indicated by a sharp change in slope of the cumulative stress relief. Cumulative stress relief continued throughout the cooling period and reached a relatively high event count, on the order of 5,000 counts, near the end of the cure cycle. The material indicated instability by its failure to reach a condition in which the stress relief events approached a zero count as the temperature of the material was cycled following cure. An early indication of this lack of stability is the continued accumulation of a relatively high number of event counts per unit time following substantially total cool down (point G).

A comparison of the signature of FIG. 4 with the signature of FIG. 3 reveals numerous differences which are indicative of the relative stability of the two specimens of composite material. The material producing the signature of FIG. 3 is relatively more stable than the material producing the signature of FIG. 4, as may be derived by the raw number of cumulative event counts, the accumulation of event counts during cure following glass transition, and the continued accumulation of event counts following cool down.

A combination of the active and passive transducer detection system allows for relatively precise identification of a number of other characteristics during the cure cycle and during thermal cycling of a composite material. An active signal, for example, is particularly useful to identify characteristics during the early stages of material formation. When coupled through the composite material during initial heat-up, an active signal falls slowly as the resin begins gelation. An increase in the active signal is observed as the resin undergoes the glass transition. Finally the peak in the active signal occurs at the cure point.

The passive signal may be observed to identify passive stress waves emitted by the composite as it approaches its cure temperature. The characteristic and frequency of the passive signals indicate the types of stress events observed.

A permanent record may be made of the cure cycle to show the level, spectrum and relative uniformity of stress relief during the cure cycle. These characteristics may be related thereafter to residual properties of the material to develop a figure of merit for the stability of the composite material.

Apparatus according to the invention can also be used to analyze stability of a composite material following full cure. For example, a specimen may be exposed to thermal and/or mechanical loading to induce stress relaxation, or cycled through a range of temperatures while the event count is monitored to observe time dependent stress characteristics indicated by acoustic signals. In this manner, a figure of merit can be developed for composite material after curing.

The invention has now been explained with reference to specific embodiments. Other embodiments and applications of the invention will be apparent to those of ordinary skill in this art upon reference to this application. It is therefore not intended that this invention be limited except as indicated by the appended claims.

I claim:

1. A method for observing potential dimensional stability of plastic composition of thermosetting material comprising the steps of:
    monitoring passive and injected acoustic signals from said composition during formation of a solid state of said composition;
    generating a signature over time from said acoustic signals, said signature being uniquely characteristic of said composition; and
    analyzing said signature to correlate with known residual stress relief mechanisms and resultant residual stress levels of said composition.

2. The method according to claim 1, further including the step of exciting said composition with a pulse train.

3. The method according to claim 1 or 2 wherein said monitoring step comprises time division multiplexing sensed injected acoustic signals which are propagated through said composition with sensed passive acoustic signals, said sensed passive acoustic signals being representative of stress relief mechanisms of said composition.

4. The method according to claim 1 wherein said injected signals are sensed only through transducer means which are subject to acoustic decoupling from said composition.

5. The method according to claim 1 or 4 wherein said passive signals are sensed through transducer means, including transducer means in acoustic contact with said composition.

6. The method according to claim 5 wherein said passive signals are sensed through transducer means also operative to sense said injected signals.

7. A method for observing potential dimensional stability of a plastic composition of thermosetting material comprising the steps of:
    exciting said composition with a pulse train;
    monitoring passive and injected acoustic signals from said composition during formation of a solid state of said
    generating a signature from said acoustic signals, said signature being uniquely characteristic of said composition, wherein said signature generating step comprising cross correlating said passive signals and injected signals.

8. A method for observing potential dimensional stability of a plastic composition of thermosetting material comprising the steps of:
    monitoring acoustic signals from said composition during post-formation conditioning of said composition;
    generating a signature over time from said acoustic signals, said signature being uniquely characteristic of said composition during said post-formation conditioning; and
    analyzing said signature to correlate with known residual stress relief mechanisms and resultant residual stress levels of said composition.

9. An apparatus for testing potential dimensional stability of a plastic composition of thermosetting material:
    means for injecting acoustic signals into said composition;
    means for monitoring passive acoustic signals and injected acoustic signals emanating from said composition as a result of a process of formation;
    means for generating a signature of said composition from said passive acoustic signals and from said injected acoustic signals, said signature being uniquely characteristic of said composition; and
    means for analyzing said signature to correlate with known residual stress relief mechanisms and resultant residual stress levels of said composition, said analyzing means being operative to compare said signature with a template representative of said known mechanisms and stress levels.

10. The apparatus according to claim 9 wherein said monitoring means includes means for monitoring acoustic signals which are provided by said injecting means through said composition, and means for independently monitoring acoustic signals which emanate from said composition independent of said signals which are provided by said injecting means.

11. The apparatus according to claim 10 including an interface means, said interface means being abutted to said composition, said interface means being acoustically separable from said composition in the process of formation of said composition, said interface means for conveying acoustic signals between said signal injecting means and said monitoring means, wherein at least one of said signal injecting means and said monitoring means is inseparably acoustically coupled to said composition throughout said process of formation and wherein the other of said signal injecting means and said monitoring means is inseparably acoustically coupled to said interface means.

12. The apparatus according to claim 10 further including an acoustically conductive interface means and wherein said means for independently monitoring acoustic signals which emanate from said composition comprises a sensor, said sensor being attached to said interface means, said interface means being subject to a physical and acoustical separating from said composition during formation and solidification of said composition, said attached sensor being operative to acoustically sense for separation between said interface means and said composition.

13. The apparatus according to claim 9 further including means for exciting said composition with a pulse train.

14. The apparatus according to claim 13 wherein said signature generating means comprising means operative to cross correlate said passive acoustic signals with said injected acoustic signals.

15. The apparatus according to claim 9 wherein said monitoring means includes means for time division multiplexing sensed injected acoustic signals which are propagated through said composition with sensed passive acoustic signals, said sensed passive acoustic signals being representative of stress relief mechanisms of said composition.

16. A method for controlling potential dimensional stability of a plastic composition of thermosetting material comprising the steps of:

injecting a first acoustic signal into said composition;

monitoring passive and injected first acoustic signals from said composition during formation of a solid state of said composition;

providing a model signature as a function of time representative of second acoustic signals propagated through and emanating from a model composition during formation of a solid state of said model composition;

comparing said first acoustic signals with said model signature to develop an error signal during formation of said composition; and modifying at least temperature of said composition during formation of said composition to minimize said error signal.

17. The method according to claim 16 wherein said injecting step comprises exciting said composition with a pulse train.

18. The method according to claim 16 or 17 wherein said monitoring step comprises time-division multiplexing a sensing of said injected acoustic signals which are propagated through said composition with a sensing of said passive acoustic signals, said passive acoustic signals being representative of stress relief mechanisms of said composition.

19. The method according to claim 18, wherein said signature generating step comprises cross correlating said time-multiplexed passive signals and injected signals.

20. The method according to claim 16 wherein said injected signals are sensed only through transducer means which are subject to acoustic decoupling from said composition.

21. The method according to claim 20 wherein said passive signals are sensed through transducer means, including transducer means in acoustic contact with said composition.

22. The method according to claim 21 wherein said passive signals are sensed through transducer means also operative to sense said injected signals.

* * * * *